United States Patent [19]

Glumac

[11] Patent Number: 4,934,383
[45] Date of Patent: * Jun. 19, 1990

[54] ELECTRODE

[76] Inventor: George Glumac, 2095 W. Hampden Ave., Englewood, Colo. 80110

[ * ] Notice: The portion of the term of this patent subsequent to Aug. 19, 2004 has been disclaimed.

[21] Appl. No.: 884,282

[22] Filed: Sep. 30, 1986

Related U.S. Application Data

[63] Continuation of Ser. No. 371,179, Apr. 23, 1982, abandoned.

[51] Int. Cl.$^5$ .............................................. A61N 1/04
[52] U.S. Cl. ..................................... 128/798; 128/802
[58] Field of Search ................................ 128/639–641, 128/798, 802, 803

[56] References Cited

U.S. PATENT DOCUMENTS

| | | | |
|---|---|---|---|
| 3,606,881 | 9/1971 | Woodson | 128/641 |
| 3,977,392 | 8/1976 | Manley | 128/641 |
| 4,207,904 | 6/1980 | Greene | 128/798 |
| 4,237,886 | 12/1980 | Sakurada et al. | 128/798 |
| 4,365,634 | 12/1982 | Bare et al. | 128/803 |

OTHER PUBLICATIONS

UNI-PATCH, "Uni-Thin Tens Electrodes", 1982.

*Primary Examiner*—Lee S. Cohen
*Attorney, Agent, or Firm*—Hugh D. Jaeger

[57] ABSTRACT

Electrode such as a TENS or post-operative electrode including a backing of plastic foam or dielectric material with an adhesive layer, an electrical communication conductor member such as a metal stud, such as of aluminum or silver, a thin polymer material with a conducting layer such as carbon or a conductive medium, an insulation retention disc coated with adhesive on both sides, a liner release, a gel protector, and an adhesive cover. The foil conductive member and polymer member are thin, providing for flexibility and low profile, and are substantially of like identical surface area. The conductive coating can be either Karaya, rodel or any conductive coating with a liner, or the user can apply a gel. The electrode is very flexible and very conforming to the surface of the skin of the individual user.

3 Claims, 4 Drawing Sheets

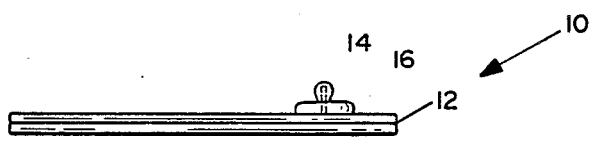
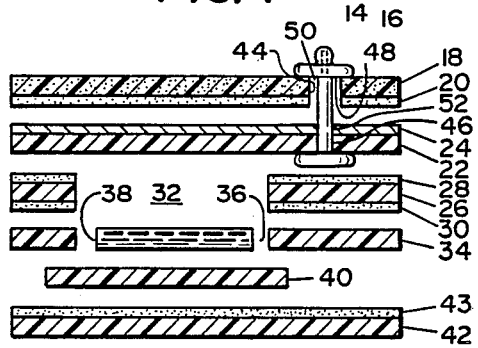
FIG. 1
FIG. 2
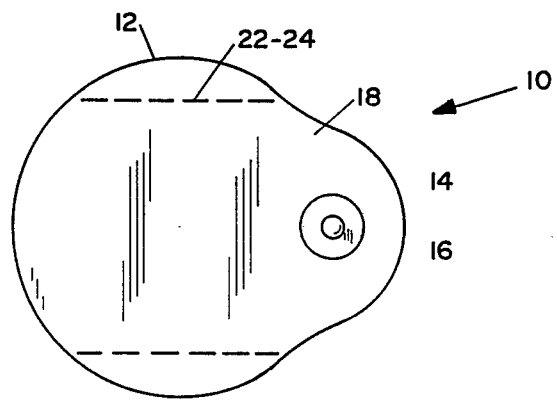
FIG. 3
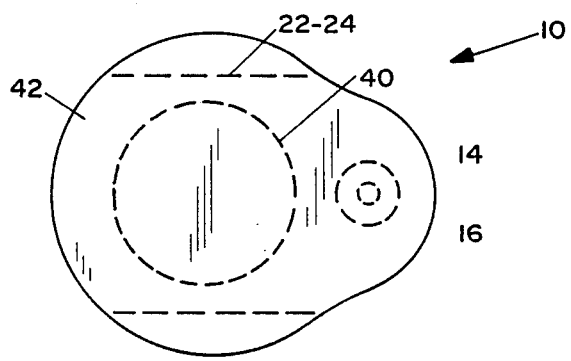
FIG. 4

ELECTRODE

CROSS REFERENCES TO CO-PENDING APPLICATIONS

This application is a continuation of application Ser. No. 371,179, filed 4-23-82, now abandoned.

BACKGROUND OF THE INVENTION

1. Field of the Invention

The present invention relates to surgery and, more particularly, pertains to an electrode for acute, chronic, and post-operative conditions to alleviate pain and enhance motor control of an individual such as through a TENS.

2. Description of the Prior Art

The prior art electrodes have failed to meet the medical needs of individuals in not providing a stimulating electrode which provides for electrical distribution of current as well as a personal comfort factor of distribution of electrical current.

The prior art stimulating electrodes have been rather complex, bulky, molded, non-flexible devices which have been less than comfortable for use by the individual patient, and in addition have provided less than equal current distribution resulting in hot or burn spots on the individual's skin from the electrode stimulation.

The prior art electrodes have been large rubber-type devices being non-flexible and having a high profile, especially noticeable under an individual's clothing, and have detracted from the medicinal purpose and benefit of the stimulating electrode. Due to the non-flexibility and bulkiness, the stimulation electrodes tend to pull away from the skin requiring adhesives of maximum adherence, thereby causing irritation and a non-comfort factor to the individual's skin. To further compound the problem, the electrodes, which tend to pull away and lift from the skin, inherently contribute to the condition by increasing the current densities at higher densities at the individual skin touching points, causing what is known in the art as "hot spots."

The prior art electrodes have failed to meet the needs of the post-operative, chronic and acute pain applications. The prior art electrodes are usually bulky, molded silicone rubber loaded with a carbon resulting in an electrode which is thicker, less flexible, and of a high impedance. In addition, the potential distribution of the electrode from the conductor drops off as a function of distance square from the point of contact to the periphery of the electrode.

The present invention overcomes the disadvantages of the prior art electrodes by providing an electrode which is low profile, includes a backing of adhesive insulator material providing for adhesion to the surface of the individual's skin, a combination of polymer film material with a metallized layer, is very flexible and very low profile whereby the metallized layer thereby provides a finite impedance for equalized current distribution. The equalized current distribution also provides for least amount of energy usage.

SUMMARY OF THE INVENTION

The general purpose of the present invention—provide an electrode which is very thin and very flexible, very low profile (and readable) manufacturable at low cost to the individual patient user, which is a prime requirement in today's world of rising medical and rising medical treatment costs. More importantly though, the electrode is very flexible and very low profile so as not to be bulky or cumbersome to the individual, thereby requiring less energy as the electrode adheres with relative ease to the skin of the individual user.

According to one preferred embodiment of the present invention, there is provided an electrode including a plurality of layers, the layers including, from top to bottom, a layer of back covering material such as plastic foam or non-foam with an adhesive layer disposed on a bottom side thereof, a layer of polymer material with a conductive layer such as aluminum or silver disposed under the layer of polymer material, the polymer film and conductive layer being substantially the same geometrical configuration, a metal eyelet engaged through a hole, engaged to the conductive layer, and secured thereto by a stud, an insulation and retention disc with adhesive engaged thereto, a release liner with gel, and an adhesive cover with a gel protector secured to the release liner whereby combination of the polymer layer and conductive layer provides for equalized current distribution and an equalized impedance for either the electrical stimulator or electrical sensor connected thereto through said electrical snap connector. The liner retains the conductive medium sterile and sealed, thereby providing a very thin, very flexible and very low profile electrode for either stimulation or sensing.

Karaya, Rodel or any conductive coating with a liner, or a gel with the release liner, can be substituted for the release liner, gel protector and adhesive cover.

A significant aspect and feature of the present invention is an electrode for either stimulation or sensing which is very thin, very flexible, very low profile and very automatable from a manufacturing process standpoint, thereby providing a medical-surgical product to the patient at a reasonable cost of treatment. More importantly though, the electrode is very thin and very flexible, conforming to the deformity in one's skin during movement and muscular action, and also has a very low profile for placement under articles of clothing.

Another significant aspect and feature of the present invention is an electrode which uses a combination of a polymer film and a conductive layer, thereby providing for equalized current distribution and homogeneous impedance over the stimulating surface of the electrode. The combination of the conductive layer and polymer film which can either be laminated together or vapor deposited provides for placement of an electrical stud anywhere on the conductive layer, thereby providing for equalized current distribution.

A further significant aspect and feature of the present invention is an electrode which is very suitable as an electrode in any predetermined configuration. While the electrode can assume any predetermined geometrical configuration such as a circle, ovoid, square, rectangle, etc., the particular disclosure here in this patent is by way of example and for purposes of illustration only, and not to be construed as limiting of the present invention.

An additional significant aspect and feature of the present invention is to provide an electrode which is very flexible and very conforming to the surface of the skin of an individual's body. The combination of the polymer layer and conductive layer provides a very unique electrode. The distributed impedance provides for equalized current distribution thereby providing for least amount of current usage.

A second alternative embodiment of the present invention includes layers of a vinyl with an adhesive coating, a carbon impregnated polymer with a vapor deposited metal coating, a vinyl-backed adhesive with a circumferential hole, Karaya, conductive gel or other non-wetting gel provided in the hold, and a liner protective cover. This provides for electrical communication between the eyelet, the metallized coating, the polymer, and the Karaya gel which can be circular or any other predetermined geometrical configuration as so punched and inserted into the double-backed adhesive vinyl member.

A first alternative embodiment of the present invention is an electrode which includes a conductive adhesive in lieu of the insulator-retainer disc, liner-release, and gel protector with an electrode gel. This provides for a different type of electrode not using a wetting gel. The layers in order include a vinyl with an adhesive coating, a carbon-filled polymer with a vapor deposited metal coating, a conductive adhesive, and a liner protective cover. The layers include two different size holes providing for electrical communication between the metallized coating and the metal eyelet, thereby exciting the polymer with electrical energy through the metallized coating in electrical communication with the metal stud.

A third alternative embodiment of the present invention includes in order: a vinyl adhesive backed member, a carbon filled polymer film, a conductive adhesive, and a liner protective cover including a stud extending through a first hole in the film and a second hole of a larger diameter than the first hole in the vinyl-adhesive layers and the vinyl-adhesive and polymer layers secured between the head of the eyelet and the stud such that the polymer carbon filled film is in electrical communication with the metal stud. Accordingly, the electrical communication occurs in order between the stud and the polymer carbon-filled film which is in engagement with the bottom side of the stud.

Having thus described embodiments of the present invention, it is the principal object hereof to provide an electrode or, more particularly, a TENS electrode.

An object of the present invention is to use the electrode in pairs in TENS applications.

Another object of the present invention is to provide a low-profile, flexible, and electrode conforming to the skin. The electrode lends itself to ease of layered assembly through manufacturing and therefore provides low cost to the patient, which is most important in today's economic times of spiraling, inflationatory medical costs in the health care product field.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 1 illustrates a side view of an electrode, the present invention;

FIG. 2 illustrates an exploded cross-sectional view of the electrode of FIG. 1;

FIG. 3 illustrates a bottom view of the electrode.

FIG. 4 illustrates a top view of the electrode;

DESCRIPTION OF PREFERRED EMBODIMENTS

Figure 5:
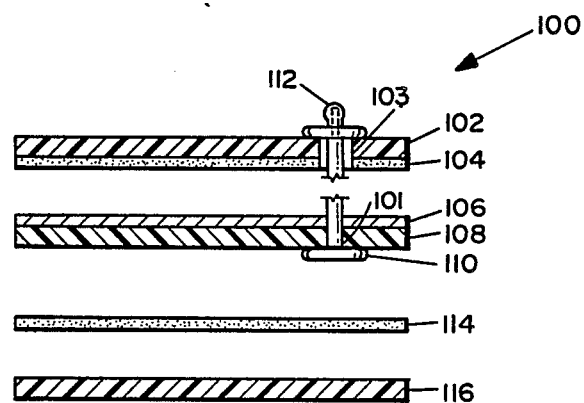
FIG. 5 illustrates an exploded cross-sectional view of a first alternative embodiment of the electrode.

FIG. 1 illustrates a side view of an electrode 10, the present invention, showing a plurality of layers 12, a plastic or metal eyelet 14 protruding therefrom, and a metal stud 16.

FIG. 2 illustrates an exploded cross-sectional view of electrode 10 of FIG. 1 including an order of the layers 12, the eyelet 14, the compression metal stud 16, a backing of foam or non-foam 18 with an adhesive layer 20, a polymer film 22 with a conductive layer 24, an insulator and retention disc 26 with adhesive 28 and 30 on each side, the disc 26 including a doughnut type hole 32, a layer 34 with a doughnut hole 36 for accommodating electrode gel 38, a cover 42 with adhesive 43 and a gel protector 40 slightly larger in diameter than the holes 32 and 36.

The layers 18, 22–24, 26, 34, and 42 have substantially the same outer diameter geometrical configuration. The electrode can assume any configuration such as rectangular, circular, ovoid, or any other predetermined shape.

Hole 44 is of a larger diameter than hole 46, where hole 44 protrudes through the vinyl foam or non-foam insulation dielectric layer 18 with adhesive coating 20. Hole 46 protrudes through the vapor deposited metallized layer 24 and the thin polycarbonate carbon impregnated film 22. The hole 44 is slightly larger than the hole 46 where the hole 46 is of a substantially identical diameter to that of the eyelet 14 which can be either metal or plastic. The stud 16 is provided with space 50 at the bottom of the stud 48. The circumferential space 50 about the bottom of the stud 48 is provided by the inherent diameter of the hole 44 so that the bottom of the stud 48 dielectrically and mechanically communicates in engagement with the top of the vapor deposited metallized layer at area 52 about circumferential radius of a small finite width of diameter within the space 50 and about the bottom of the stud 48. This engagement between the bottom of the stud 48 and the metallized layer 24 about the circumferential area 50 provides dielectrical communication and provides the low profile flexibility of the electrode. A suitable electrode wire connects against the stud 16 by a snap such as a plastic snap over the eyelet 14, as is known in the art.

The electrode 10 is comprised of layers of the following material. The vinyl 18 with adhesive layer 20 is a "3M" formula vinyl "711" with a thin layer of medical adhesive coated thereon. The polymer film with a conductive layer 22–24 is a polycarbonate carbon impregnated film of 0.00075 inches thick polycarbonate carbon impregnated film with 1500 Å vapor deposited metal layer of zinc. This material is manufactured to specifications by Kimberly-Clark. The metal eyelet 14 and stud 16 are commonly available such as from TRW. The retaining disc is again the 3M vinyl material with adhesive coated on both sides. The liner 34 is a high-density polyethylene silicone coated release liner for use in both a pre-gel and user-gelled electrode, the gel protector 40 is the 3M vinyl material, and the adhesive cover is the 3M vinyl material with adhesive coating. The layers 34, 40 and 42 including the adhesive backing 44 comprise one peel-away member when pre:-gel is used. The pre-gel can be such a gel as Lectron III by Pharmaceutical Innovations. In the event the electrode is not pre-gelled, any suitable adhesive coating or conductive coating such as Karaya or Rodel can be utilized in lieu of layers 34, 40 and 42. Alternatively, a user may apply gel over the exposed polymer film, at which time a continuous release liner 34 without a doughnut hole 36 can be utilized to protect the insulator-retention disc and polymer film.

Electrical communication occurs between a wire such as that connected to a TENS unit, the wire not shown for sake of brevity and clarity in the drawing, through the metal stud 16 which is in engagement about a circumferential compressed area 50 with the vapor deposited metallized layer 24. Whether the eyelet 16 is metal or plastic, the eyelet only serves to hold the metallized layer 24 in electrical communication with the metal stud 16.

FIG. 3 illustrates a top view of the electrode where all numerals correspond to those elements previously described. Attention is drawn to the metal stud and engaging eyelet 16.

FIG. 4 illustrates a bottom view of the electrode where all numerals correspond to those elements previously described.

MODE OF OPERATION

The electrode 10 of the present invention is utilized usually in pairs where the electrodes are positioned by removing the liner adhesive cover 42 carrying the gel protector 40 and positioning the electrodes at the desired point of the body. Subsequently, conductors are connected to the metal eyelet and communication is commenced. The electrodes, for example, might be positioned on either side of a surgical incision on an individual's body to alleviate pain and enhance healing about that incision or incisions, or may be positioned at points of pain.

In the event where the electrode 10 is used in a sensing mode of operation, any number of electrodes can be utilized and are positioned at predetermined sensing sites.

The electrodes can be packaged in a sterile package as known in the art.

The stud and eyelet perform a two-fold function in holding the layers together, specifically 22-24 and 18-24, and in providing for electrical communication between the bottom of the eyelet and the metalized layer 24 which excites the polymer film 22 which is loaded with carbon or conducting material. The free space about the second hole in the layers 18-20 provides for the communication with the bottom of the stud 48 in the compressed area 50. While the electrode has been illustrated in an exploded view, in operation, all layers are touching and compressed and the bottom 48 of the stud 16 touches the layer 24 about the area 50 when the layers are secured by the adhesive and compressed by the stud-eyelet function. The electrode then takes the appearance of FIG. 1. Inherently, the members, especially 22-24 are thinner than paper by comparison.

FIRST ALTERNATIVE EMBODIMENT OF PRESENT INVENTION

FIG. 5 illustrates a first alternative embodiment 100 the present invention showing an exploded cross-sectional view including vinyl 102; adhesive 104; carbon filled polymer film 108; vapor deposited metallized coating 106 such as zinc, aluminum, silver or the like; stud 110 protruding through a first hole in layers 106 and 108, through a second hole 102 and 104 of a larger diameter than said first hole; eyelet 112; conductive adhesive 114; and liner protective cover 116. The conductive adhesive 114 can be Rodel or Karaya or any other suitable like adhesive. All other components are similar to those previously described.

In operation, electrical communication is established between the space by the second larger hole and the layers 102 and 104 between the eyelet 112 and the metal layer 106.

SECOND ALTERNATIVE EMBODIMENT OF PRESENT INVENTION

Figure 6:
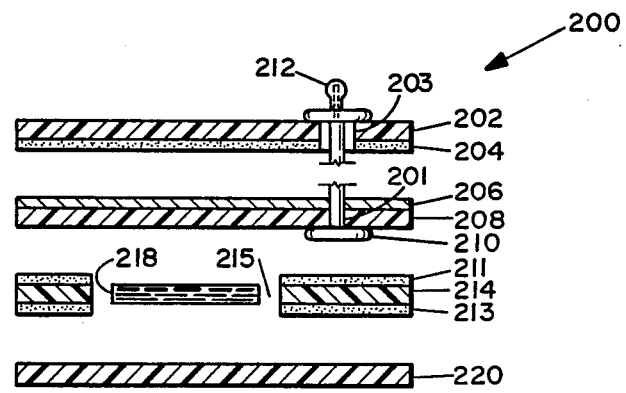
FIG. 6 illustrates an exploded cross-sectional view of a second embodiment of the electrode; and, FIG. 7 illustrates an exploded cross-sectional view of a third embodiment of the electrode.

FIG. 6 illustrates an exploded cross-sectional view of an electrode 200 including in order vinyl insulator 202, adhesive coating 204 thereon, polymer carbon impregnated film 208 with a vapor deposited metal coating 206, stud 210 through a first hole 201 in layers 206-208 and a second larger hole 203 including a hole 215, Karaya or conductive gel or a non-waterable gel 218 in the hole 215 and of a substantially like diameter as that of the hole, and a protective liner 220. Eyelet 212 secures over eyelet 210.

Operation is similar to that described for the previous figures where electrical communication is established between the metallized layer 206 and the metal stud 218 about the larger diameter circumferential space in the layer 202-204.

THIRD ALTERNATIVE EMBODIMENT OF PRESENT INVENTION

Figure 7:
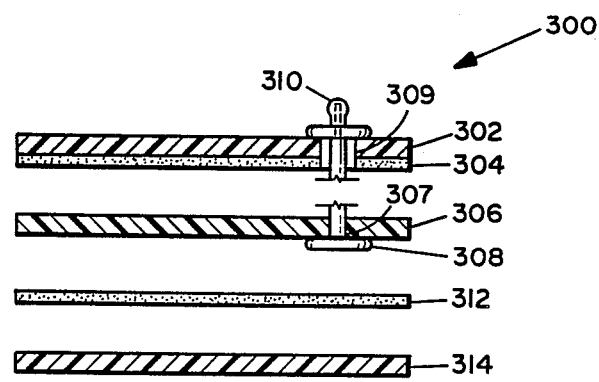

FIG. 7 illustrates an exploded cross-sectional view of electrode 300, a third alternative embodiment of the present invention, showing vinyl layer 302 with adhesive coating 304, a carbon-filled polymer film 306, a stud 308 protruding through a first hole in the film 308 and a second hole in the layer 302-304, the second hole 309 larger in diameter than the first hole 307, an eyelet 310, a conductive adhesive 312 positioned over the film 306, and a protective liner cover 314. This particular embodiment shows that there is electrical communication between the eyelet 310 and the carbon-filled polymer film 306 about the circumferential space provided by the second larger hole and the vinyl-adhesive layer 302-304.

Operation of this embodiment of the electrode is similar to that of electrodes previously described.

Various modifications can be made to the electrode of the present invention without separating from the apparent scope thereof.

Having thus described the invention, what is claimed is:

1. Electrode comprising:
   a. vinyl backing material including a layer of adhesive disposed over a bottom portion thereof and of a first outer diameter and including a first eyelet opening;
   b. conductive thin polycarbonate carbon impregnated film including a vapor deposited metalized layer disposed on a top side thereof and of said first outer diameter, said metalized layer adhering to said adhesive of said backing material and including a second eyelet opening;
   c. insulating retention disc including an internal opening of a round hole of a second diameter, said second diameter being less than said first diameter, adhesive positioned on both sides thereof and said disc being of said first outer diameter, said disc adhering to said film by said adhesive on one side of said disc and including a conductive gel in the opening of said disc;

d. eyelet extending through said second eyelet opening through said film with said metalized layer and through said first eyelet opening in said backing material, said first opening slightly larger in diameter than said second opening, said eyelet including a flat base member which engages in electromechanical contact against said film; and, e. metal stud electromechanically secured over said eyelet and holding in engagement said thin film and said metalized layer and said backing layer, a bottom side of said metal stud electrically and mechanically communicates in engagement with a top area of said metalized film about a circumference radius of said metal stud in an area provided between difference in area of said second and first openings whereby said electrode is low profile and flexible, thereby providing consistent conformity on placement on an individual's skin.

2. Electrode of claim 1 comprising:

a. release layer including top and bottom surfaces, said top surface being supported on said adhesive side of said disc opposite said side of said film support, said release layer including a like geometrical configuration of said first outer diameter of said insulating retention disc, and including an opening of a round hole of said second diameter;

b. gel protector having a slightly larger geometrical shape than said opening of said second diameter in said release layer and supported on a bottom surface of said release layer and forming a pocket about a hole of a second diameter in said release layer; and, c. covering including adhesive on a top side thereof supported on the bottom surface of said release layer by said adhesive on said top side thereof and of said first outer diameter whereby said adhesive covering and release layer encompass said gel protector, and said gel protector holding and protecting gel held within said pocket formed in said insulating retention disc.

3. Electrode of claim 1 comprising:

a. cover of said first outer diameter disposed over said insulating retention disc, over said adhesive on the side of said disc opposite the side of said film support whereby said cover protects said electrode.

* * * * *